US00PP11020P

United States Patent [19]

Evers

[11] Patent Number: Plant 11,020

[45] Date of Patent: Aug. 3, 1999

[54] HYBRID TEA ROSE PLANT NAMED 'TANETTOLA'

[75] Inventor: Hans-Jürgen Evers, Uetersen, Germany

[73] Assignee: Bear Creek Gardens, Inc., Medford, Oreg.

[21] Appl. No.: 08/986,715

[22] Filed: Dec. 8, 1997

[51] Int. Cl.[6] ..... A01H 5/00

[52] U.S. Cl. ..... Plt./20

[58] Field of Search ..... Plt./20, 21

*Primary Examiner*—Howard J. Locker

*Attorney, Agent, or Firm*—Klarquist Sparkman Campbell Leigh & Whinston, LLP

[57] ABSTRACT

Hybrid tea rose plant having good cut flower production of bright red flowers on long, strong stems with good cut flower vase life.

1 Drawing Sheet

The present invention relates to a new and distinct variety of rose plant of the hybrid tea class which was originated by me by crossing the variety 'KORlingo,' U.S. Plant Pat. No. 5,846, with the variety 'Roulette', (unpatented).

The primary objective of this breeding was to produce a new rose variety having the bright red flower color and good cut flower production of the female parent combined with the long stems of the male parent. The objective was substantially achieved, along with other desirable improvements, as evidenced by the following unique combination of characteristics that are outstanding in the new variety and that distinguish it from its parents, as well as from all other varieties of which I am aware:

1. Good cut flower vase life;
2. Bright red flowers;
3. Good cut flower production with long, strong stems.

'TANettola' was bred and selected to be a cut rose. Stems are long and strong, averaging 24 inches or more. Production in Southern California is 160-180 stems per square meter of greenhouse or about 24-25 marketable flowers per plant.

Asexual reproduction of this new variety by budding, as performed at Uetersen, Germany and Wasco, Calif., shows that the foregoing and all other characteristics and distinctions come true to form and are established and transmitted through suceeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORlingo (U.S. Plant Pat. No. 5,846).

*Pollen parent.*—Roulette (unpatented).

Classification:

*Botanical.*—*Rosa hybrida.*

*Commercial.*—Hybrid Tea.

FLOWER

Observations made from specimens grown in a greenhouse environment at Uetersen, Germany and at Somis, Calif. from January, 1996–August, 1997.

Blooming habit: Continuous.

Bud:

*Size.*—One and three-quarter inches long when the petals start to unfurl.

*Form.*—The bud form is long, pointed ovoid.

*Color.*—When sepals first divide, bud color is Red Group 46A with some blackening at petal tips. When half blown, the upper sides of the petals are Red Group 45B; and the lower sides of the petals are Red Group 53B.

*Sepals.*—Color: Green group 138B. Surface texture: Covered in fine hairs. There are three normally to heavily appendaged sepals. There are two unappendaged sepals with hairy edges.

*Receptacle.*—Color: Yellow-Green Group 144A. Shape: Funnel. Size: Medium (⅜"×¼"). Surface: Smooth.

*Peduncle.*—Length: Medium (3½" to 4"). Surface: Smooth with a few small prickles. Color: Light green. Strength: Stiff, erect.

Bloom:

*Size.*—Large. Average open size is 4 inches.

*Borne.*—Singly.

*Stems.*—Long (22–26"), strong.

*Form.*—When first open: High centered. Permanence: Retains its form to the end; outer petal edges curl back, some quilling.

*Petalage.*—Number of petals under normal conditions: 30.

*Color.*—The upper sides of the petals are Red Group 45B. The reverse sides of the petals are Red Group 53B. The base of each petals has a small (7/32"×5/32"), yellow (Yellow Group 5A) half moon at the point of attachment. The major color on the upper sides is Red Group 45B.

*Variegations.*—None.

*Discoloration.*—At the end of the first day: No change. At the end of the third day: No change. By day six on the plant the flower fades to Red Group 45D.

*Fragrance.*—Slight.

Petals:

*Texture.*—Thick, leathery.

*Shape.*—Round.

*Form.*—Tips slightly recurved, edges slightly quilled.

*Arrangement.*—Imbricated. Petaloids in the center are few.

*Persistence.*—Drop off cleanly.

*Lastingness.*—On the plant: Long (seven days). As a cut flower: Long (ten to twelve days).

Reproductive parts:

*Anthers.*—Size: Medium. Quantity: Many. Color: Yellow. Arrangement: Regular around styles.

*Filaments.*—Color: Reddish brown.

*Pollen.*—Color: Gold yellow.

*Styles.*—Color: Reddish purple.

*Stigmas.*—Color: Greenish-white.

Plant:

*Form.*—Bush.

*Growth.*—Very vigorous; upright; branching; In six months of growth in a greenhouse in Somis, Calif., 'TANettola' reached a height of six feet. Through regular harvest of flowering stems, it may be kept at this height.

*Foliage.*—Number of leaflets on normal mid-stem leaves: Five or seven.

*Size.*—Large. (5–6"×4–5").

*Quantity.*—Normal.

*Color.*—New foliage: Greyed-Red Group 178B but quickly becoming green. Old foliage: Upper surface: Green Group 139A. Lower surface: Green Group 139C.

*Shape.*—Pointed oval.

*Texture.*—Upper side: Smooth.

*Edge.*—Serrated.

*Serration.*—Single, small.

*Petiole rachis.*—Color: Green with some red.

*Petiole underside.*—Rough, with several prickles.

*Stipules.*—Long (¾"); serrated, bearded.

*Disease resistance.*—Susceptible to mildew under normal growing conditions at Somis, Calif. No other disease tested.

Wood:

*New wood.*—Color: Light green. Bark: Smooth.

*Old Wood.*—Color: Green. Bark: Smooth.

Prickles:

*Quantity.*—On main canes from base: Ordinary. On laterals from main canes: Ordinary.

*Form.*—Medium (⅜"); straight to hooked slightly downward.

*Color when Young.*—Red.

Small Prickles:

*Quantity.*—On main stalks: None. On laterals: None.

I claim:

1. A new and distinct variety of rose plant of the hybrid tea class, substantially as herein shown and described, characterized particularly as to novelty by good cut flower production with long, strong stems; bright red flower color; and good cut flower vase life.

* * * * *

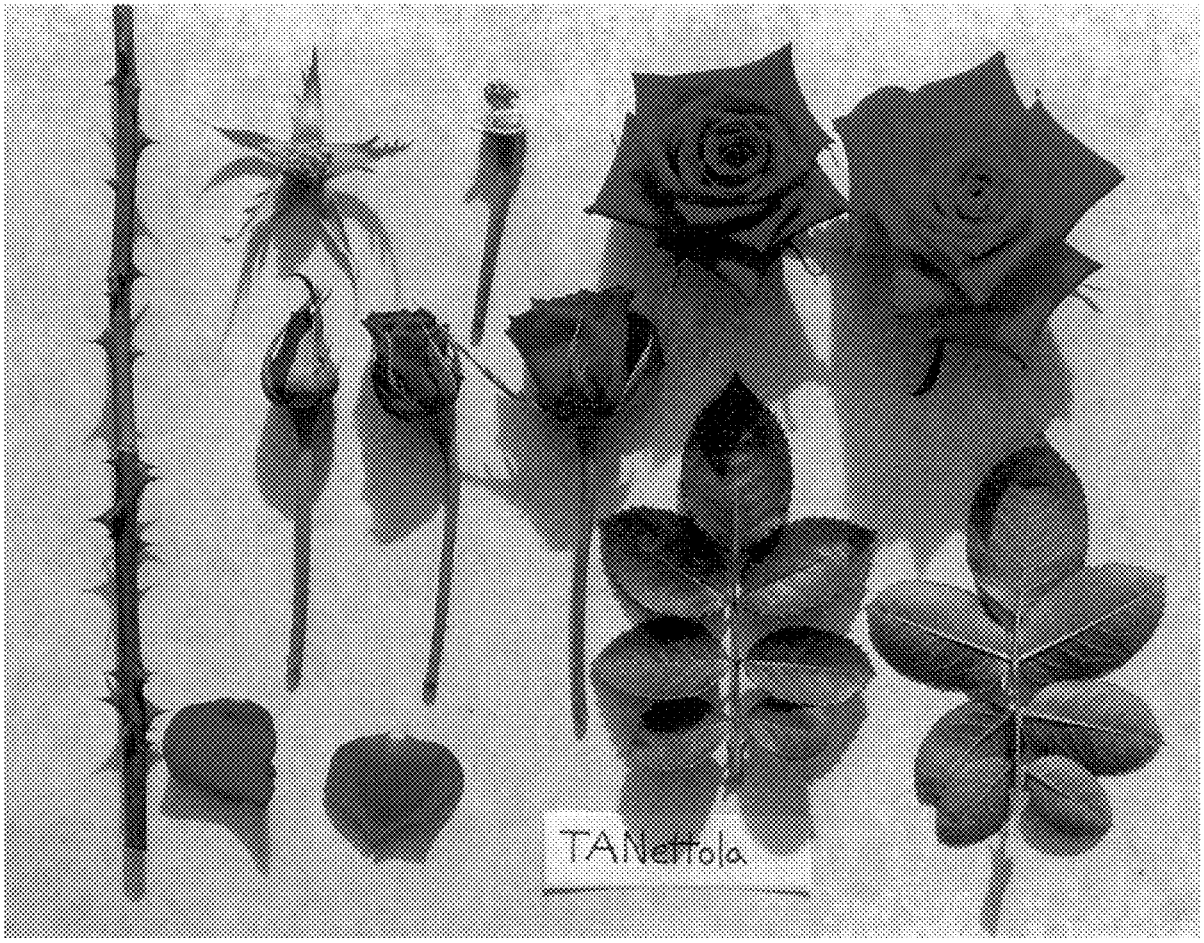
TANettola